United States Patent [19]

Gay

[11] 4,079,139

[45] Mar. 14, 1978

[54] FLAVONE DERIVATIVES

[75] Inventor: Allesandro Gay, Cinisello Balsamo (Milan), Italy

[73] Assignee: Farmalepori, Barcellona, Spain

[21] Appl. No.: 602,802

[22] Filed: Aug. 7, 1975

[30] Foreign Application Priority Data

Aug. 13, 1974 United Kingdom .............. 35600/74

[51] Int. Cl.$^2$ ................. C07D 405/10; A61K 31/535; C07D 407/10
[52] U.S. Cl. ............................... 424/248.58; 424/267; 424/274; 424/283; 260/293.58; 260/326.5 CA; 260/345.2; 544/151
[58] Field of Search ................... 260/247.5 H, 293.58, 260/326.5 CA, 345.2; 424/267, 248, 274, 283, 248.58

[56] References Cited

U.S. PATENT DOCUMENTS 3,147,258  9/1964  Re et al. ........................... 260/293.58

FOREIGN PATENT DOCUMENTS 1,300,726  7/1962  France ............................. 260/345.2

OTHER PUBLICATIONS

Chapman et al., "J. Chem. Soc.," vol. 123, pp. 404–409, (1923).
Baker et al., "J. Chem. Soc.," vol. 127, pp. 1981–1986, (1925).
Shriner et al., "J. Org. Chem.," vol. pp. 228–231, May, 1945.
Re et al., "Arnezmittle Forschuna," International Edition, vol. 10, pp. 800–802, (1960).

*Primary Examiner*—Natalie Trousof
*Assistant Examiner*—Robert T. Bond
*Attorney, Agent, or Firm*—Farrell R. Werbow

[57] ABSTRACT

New flavone derivatives to be used as analeptics having the formula

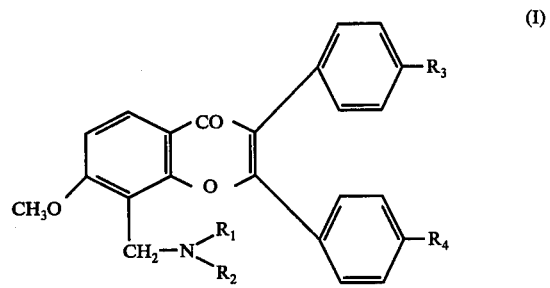

wherein $R_1$ and $R_2$ are both methyl or ethyl, or taken together with the nitrogen atom to which they are attached represent a mononuclear 5- or -6 membered heterocyclic ring which may contain an oxygen atom as further hetero atom; $R_3$ and $R_4$ are hydrogen or methyl, provided that at least one of them is hydrogen, and process for the preparation thereof starting from resorcinol and phenylacetonitrile or a phenylacetonitrile derivative.

6 Claims, No Drawings

FLAVONE DERIVATIVES

This invention relates to new flavone derivatives, to a new process for their preparation and to pharmaceutical compositions containing them.

According to the present invention, there are provided the new flavone derivatives of the general formula

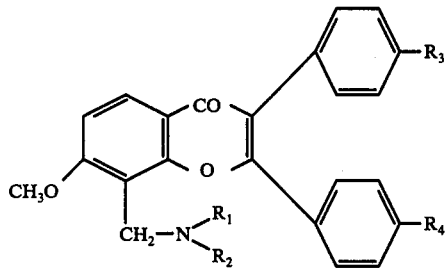

wherein $R_1$ and $R_2$ are both methyl or ethyl, or taken together with the nitrogen atom to which they are attached represent a mononuclear 5- or -6 membered heterocyclic ring which may contain an oxygen atom as further hetero atom; $R_3$ and $R_4$ are hydrogen or methyl, provided that at least one of them is hydrogen.

According to a feature of the present invention the compounds of formula (I) are prepared through a multi-step process, starting from resorcinol, as more specifically indicated hereinafter:

a. resorcinol is made to react with phenylacetonitrile or suitable phenylacetonitrile derivative in an organic solvent (preferably ethyl ether) while adding powdered $ZnCl_2$ and saturating with gaseous HCl.

The thus formed keto-imine hydrochloride is boiled with water and poured into NaOH wherefrom the 2.4-dihydroxy-acetophenone derivative is precipitated by addition of HCl.

The overall reaction may be schematically represented as follows:

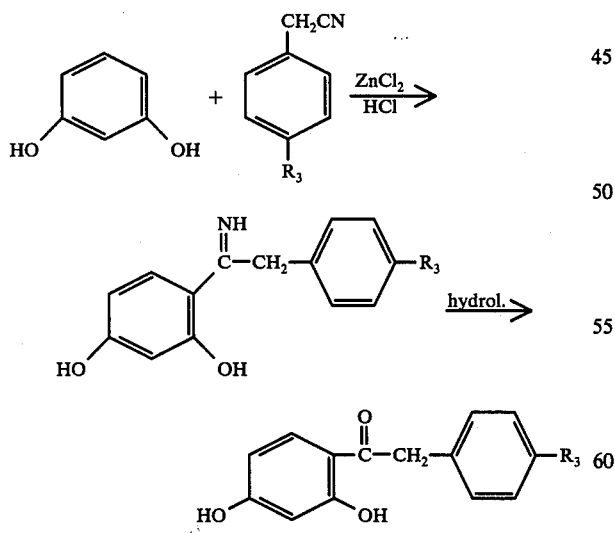

where $R_3$ is hydrogen or methyl.

b. The 2.4-dihydroxy-acetophenone derivative is fused with a mixture of sodium benzoate and benzoic anhydride or with a mixture of the corresponding salt and anhydride where the phenyl ring brings the desired substituent group. The fused mass is dissolved in boiling ethanol and water and from the solution the 7-hydroxy-flavone derivative is precipitated with an alkaline carbonate.

This step may be schematically indicated as follows:

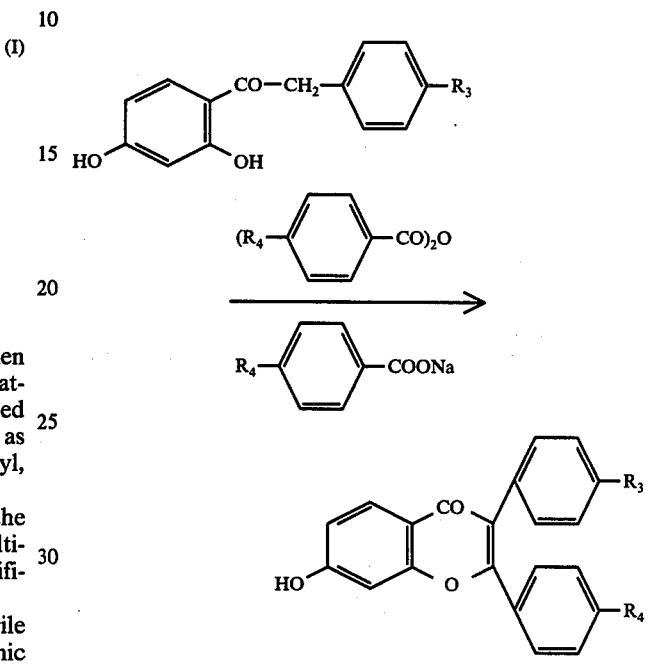

where $R_4$ is hydrogen, methyl or halogen atom.

c. The 7-hydroxy group present in the last prepared compound is changed in a methoxy group by reaction with dimethylsulphate in the presence of potassium carbonate.

The reaction involved is the following one:

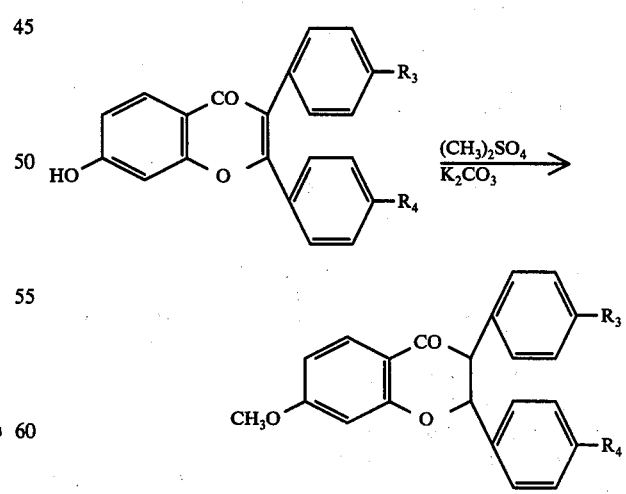

d. The flavone derivative obtained in step (c) is made to react with formaldehyde and hydrochloric acid in the presence of acetic acid, so as to introduce a chloromethylen group in the 8-position

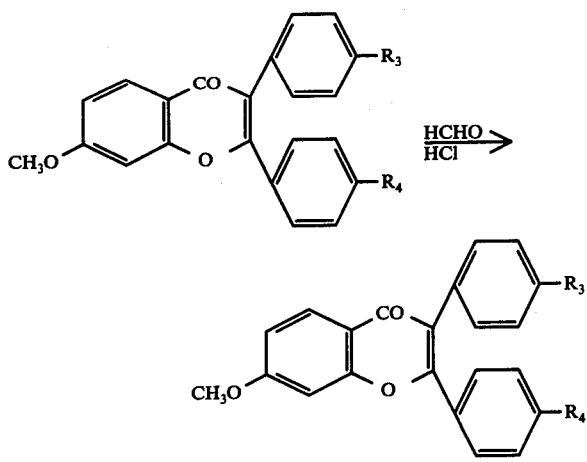

e. Finally the nitrogen containing basic group is introduced in the molecule, by reaction with the desired base in an organic solvent solution

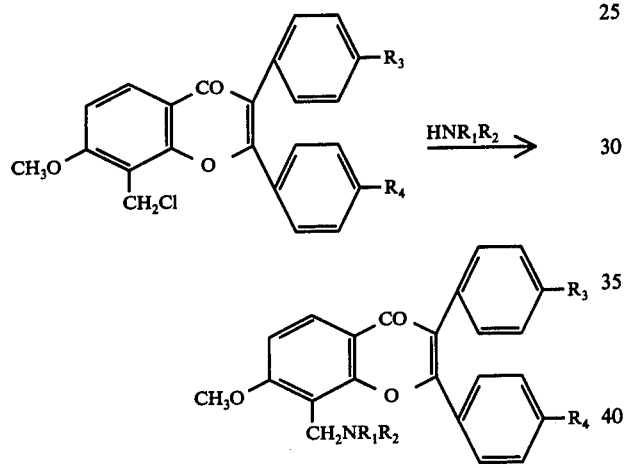

Successively the flavonic base may be salified with any desired organic or inorganic acid.

A number of variations may be introduced in the above process, all at the hand of a man skilled in the art and thus all comprised in the field of the invention.

Some preparative examples are reported hereinafter in order to better clarify the manner of practically reproducing the present invention.

EXAMPLE 1

Resorcinol (110 g) and p.tolylacetonitrile (131 g) are dissolved into 400 ml of anhydrous ethyl ether and added with 20 g of powdered $ZnCl_2$. The solution is saturated with gaseous HCl and allowed to rest over two days. 400 ml of ether are further added and the organic layer is removed to remove the unreacted and by-products compounds.

The oleous layer consisting of the keto-imine is added with 500 ml of water and allowed to boil for two hours. The product is extracted with $CHCl_3$ and poured in 1N NaOH wherefrom it is precipitated with diluted HCl and finally crystallized from benzene.

Twenty grams of the thus prepared 2',4',-dihydroxy-2-(p.tolyl)-acetophenone are admixed with 100 g of benzoic anhydride and 10 g of sodium benzoate and the mixture is heated at 180°-190° C over 12h. After this time the mass is dissolved into 250 ml of ethanol and 50 ml of water, and the solution is kept under boiling for a few minutes.

Then a solution of 60 g KOH in 100 ml of water is added and the whole is heated over 15 minutes before diluting with 500 ml of water. Upon bubbling $CO_2$ in the solution the compounds 7-hydroxy-3-(p.tolyl)-flavone precipitates which is filtered and crystallized from ethanol.

Four grams of 7-hydroxy-3-(p.tolyl)-flavone are dissolved into 60 ml of anhydrous acetone, added with 2 g of dimethylsulphate, 3 g of $K_2CO_3$ and refluxed over 7 hours. After cooling, the formed precipitate is filtered and washed with acetone. The 7-methoxy-3-(p.tolyl)-flavone thus formed is further crystallized from ethanol.

A mixture consisting of 3 g of 7-methoxy-3-(p.tolyl)-flavone, 30 ml of acetic acid, 8.5 ml of a 40% aqueous formaldehyde solution is heated for 7h in a gaseous HCl stream. The reaction mixture is poured in ice water and left overnight.

The compound 7-methoxy-8-chloromethyl-3-(p.tolyl)-flavone precipitates which is filtered, washed with water, dried and crystallized from ethanol.

Five grams of 7-methoxy-8-chloromethyl-3-(p.tolyl)-flavone and 4 ml of morpholine dissolved into 100 ml of anhydrous ethanol are refluxed over 6h.

Upon cooling the 7-methoxy-8-morpholinomethyl-3-(p.tolyl)-flavone crystallizes which is purified by recrystallization from ethanol M.P. 202°-205° C(dec.)

EXAMPLE 2

Resorcinol (110g) and phenylacetonitrile (117 g) are dissolved into 400 ml of anhydrous ethyl ether and added with 20 g of powdered $ZnCl_2$.

The solution is saturated with gaseous HCl and allowed to stand over 2 days.

400 ml of anhydrous ethyl ether are added and the separated oleous layer is added with water (500 ml) and kept under boiling over 2 h. The product extracted with $CHCl_3$ is poured in a 1 N NaOH solution wherefrom it is precipitated by addition of diluted HCl.

The 2',4'-dihydroxy-2-phenylacetophenone precipitates which may be purified by crystallization from benzene.

Twenty grams of 2',4'-dihydroxy-2-phenylacetophenone, admixed with 100 g of toluic anhydride and 10 g of toluic acid sodium salt are heated at 180°-190° C over 12h. After this time the solid mass is added with 250 ml of ethanol and 50 ml of water and the whole is kept under boiling for a few minutes.

A solution consisting of 60 g of KOH into 100 ml of water is added, the whole is heated over 15 minutes and then diluted with 500 ml of water. Upon bubbling in the solution $CO_2$, the compound 7-hydroxy-2-(p.tolyl)-isoflavone precipitates.

Four grams of 7-hydroxy-2-(p.tolyl)-isoflavone are dissolved into 60 ml of anhydrous acetone together with 2g of dimethylsulphate in the presence of 3g of $K_2CO_3$.

The whole is refluxed over 7h.

The precipitate formed after cooling is filtered, washed with acetone and dried under vacuum.

The residue constituted by 7-methoxy-2-(p.tolyl)-isoflavone is crystallized from ethanol.

A mixture consisting of 7-methoxy-2-(p.tolyl)-isoflavone (3g), 30 ml of conc.HCl, 30 ml of acetic acid and 8.5 ml of a 40% aqueous formaldehyde solution is heated at 70° C, over 7h under gaseous HCl stream.

The reaction mixture is poured in ice water and allowed to stand overnight. The separated solid is filtered, washed with water, dried and crystallized from ethanol. It is obtained 7-methoxy-8-chloro-methyl-2-(p.tolyl)-isoflavone.

Five grams of 7-methoxy-8-chloromethyl-2-(p.tolyl)-isoflavone are dissolved into 100 ml of ethanol containing 2g of dimethylamine and heated at 50° C over 6 h.

The solution is evaporated to dryness and the residue is taken up with $CHCl_3$. The chloroformic solution is extracted with acid water and the compounds 7-methoxy-8-dimethylamino methyl-2-(p.tolyl)isoflavone (M.P. 163°–164° C) precipitates by alcalinization of the aqueous layer.

EXAMPLE 3

5 g of 7-methoxy-8-chloromethyl-3-p.tolylflavone prepared as described in example 1, are treated under reflux conditions with 4 g of piperidine dissolved into 150 ml of anhydrous ethanol. Heating is continued over 6 hours. At this moment the solution is brought at +5° C and left at this temperature over 12 hours. The formed crystalline mass is filtered and recrystallized from ethanol.

4 g of 7-methoxy-8-piperidinomethyl-3-(p.tolyl)flavone are obtained, having a M.P. 175° – 178° C with decomposition.

EXAMPLE 4

5 g of 7-methoxy-8-chloromethyl-3-p.tolylflavone prepared as described in example 1, are treated under reflux conditions with 4 ml of pyrrolidine dissolved into 150 ml of anhydrous ethanol. After 1 hour the solid is completely dissolved and heating is continued over 5 hours. At this moment the mass is collected at +5° C and is allowed to crystallize over 12 hours.

The crystalline mass is filtered and recrystallized from ethanol. 3.3g of 7-methoxy-8-pyrrolidinomethyl-3-(p.tolyl)flavone are obtained, having a M.P.168° C.

EXAMPLE 5

5 g of 7-methoxy-8-chloromethyl-3-p.tolylflavone prepared according to example 1, are suspended into 150 ml of ethanol; the whole is cooled on ice and 4 g of gaseous dimethylamine are bubbled in the suspension. The mixture is kept under stirring, at 0° C, over 3 hours; then the temperature is raised at 20° C and maintained at this value over 12 hours. A clear solution is obtained. By cooling at 0° C a solid precipitates which is filtered: 2 g of 7-methoxy-8-dimethylaminomethyl-3-(p.tolyl)flavone are obtained with a M.P.180° C.

From the mother liquors further 1.7 g of product at M.P.180° C are obtained.

EXAMPLE 6

5 g of 7-methoxy-8-chloromethyl-3-p.tolylflavone prepared according to Example 1, and 4ml of diethylamine are admixed with 150 ml of ethanol.

The mixture is heated at 50° C over 12 hours, then the solvent is evaporated to dryness, the residue is taken up with chloroform and washed with a 5% solution of $Na_2CO_3$. From the chloroform phase, 1.3 g of 7-methoxy-8-diethyl aminomethyl-3-(p.tolyl)flavone with a M.P. 138° C are obtained. Still 2.5 g of the same product are recovered from the mother liquors.

EXAMPLE 7

The 7-methoxy-8-chloromethyl-2-(p.tolyl)-isoflavone prepared according to example 2, is made to react with piperidine as described in example 3 for the corresponding flavone compound. The 7-methoxy-8-piperidinomethyl-2-(p.tolyl)isoflavone is obtained.

EXAMPLE 8

The 7-methoxy-8-chloromethyl-2-(p.tolyl)-isoflavone prepared according to example 2, is made to react with pyrrolidine as described in example 4 for the corresponding flavone compound. The 7-methoxy-8-pyrrolidinomethyl-2-(p.tolyl)isoflavone is obtained.

EXAMPLE 9

The 7-methoxy-8-chloromethyl-2-(p.tolyl)-isoflavone prepared according to example 2, is made to react with diethylamine as described in example 6 for the corresponding flavone compound. The 7-methoxy-8-dietylaminomethyl-2-(p.tolyl)isoflavone is obtained.

The new compounds of the invention have proved to possess, both in pharmacological and in clinical tests, a stimulating activity on the CNS and a very low toxicity. These characteristics render the new compounds extremely interesting as analeptics. While a number of analeptics are presently known, their use in human therapy to antagonize respiratory depression and poisoning from barbiturates, has been remarkably reduced in the last years just due to their toxicity, to their convulsivant activity and in general to the induced side-effects.

In order to better point out the strong progress brought in the field of analeptics by the new compounds of the invention, some relevant pharmacological data are given hereinafter in comparison with the equivalent data for Dimefline ("The Merck Index" 8th Edition page 371), the best analeptic presently known and also the most similar from the point of view of chemical structure.

For the sake of simplicity we will report hereinafter only the pharmacological data for the compound:

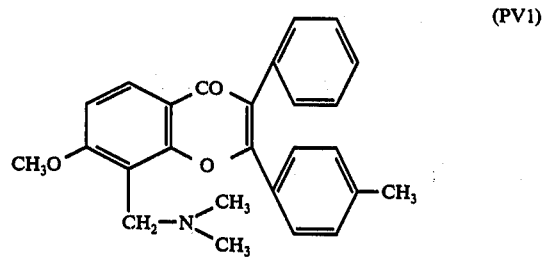
(PV1)

The identical screening has been performed also with all the compounds prepared according to the examples precedently given.

It has been found that the methyl-flavones and the methyl-isoflavones have an activity identical to that of PV1. Accordingly for all these compounds an $ED_{50}$ of 5mg/kg has been determined.

It has been also found that unsubstituted flavones ($R_3 = R_4 = H$) have an activity of 10–12% lower than that of PV1 and thus an $ED_{50}$ value comprised between 5,5 – 5,6 mg/kg.

What regards the toxicity, all the methyl-isoflavones ($R_4 = CH_3$) have the same toxicity than the compound PV1, while the methylflavones ($R_3 = CH_3$) and the unsubstituted flavones have a toxicity of 10-20% higher than that of PV1.

Moreover the following pharmacological tests have been performed, being understood that what said for PV1 is equally true for the remaining compounds, under the above provisions.

1. Acute toxicity in mouse and rat.

The test has been performed on Swiss mice of the weight of 20-22 g and on rats Sprague-Dauley of the weight of 120-130 g, subdivided in groups comprising 5 male and 5 female animals. The new drugs have been administered to animals hungry since 15-18 hours, both by oral and i.p.route. The $LD_{50}$ values have been determined according to Litchfield and Wilcoxon (J.Pharmacol.96,99,1949). The results are reported in the following Table 1, in comparison with $LD_{50}$ value for Dimefline.

TABLE 1
Acute toxicity

| Animals/ dose | Drug | route | mg/KG Administration | $LD_{50}$ and F.L. |
|---|---|---|---|---|
| Mouse 50 + 50 | PV$_1$ | os | | 80.0 (61.6–104) |
| | | i.p. | | 28.2 (20.1–39.5) |
| Mouse* | Dimefline | os | | 11.9 (10.3–13.8) |
| | | i.p. | | 4.8 (4.6–5.0) |
| Rat 50 + 50 | PV$_1$ | os | | 76.4 (63.8–13.8) |
| | | i.p. | | 22.5 (16.0–31.5) |

*Setnikar e coll. - J.Pharmacol.128, 176, 1960

It is apparent that the compound PV1 (and thus all the compounds of the present invention) is by far less toxic than Dimefline.

2° Chronic toxicity in rat.

To perform this test, 36 Sprague-Dauley rats of the average weight of 120 g have been used. The rats have been subdivided in 3 groups, each comprising an equal number of male and female animals, and have been all kept under standard conditions of environment and diet.

One group has been kept as the control while the remaining two groups have been treated with PV1 in the amount of 5 and 10 mg/kg, corresponding respectively to ⅛ and 1/8 of the $LD_{50}$ for this peculiar species.

The treatment has been repeated 5 times/week over 12 weeks by means of gastric probe and the animals have been constantly kept under control.

The result of the controls performed during and after the tests are summarized in the Tables 2, 3, 4, 5.

No death has been registered during or at the end of the test.

No intolerance of the drug has been noted.

The data collected show that the increase in the weight of the treated animals is identical to that of the controls. Also the remaining hematologic and hematochemical tests do not show significant difference between controls and treated animals.

The autopsy has revealed no lesion of the different organs.

Table 2
Chronic Toxicity in rat and hematologic tests.

| Number of animals. | mg/Kg | Weeks of treat. | Hemazies $10^6/mm^3$ | Leucocytes $10^3/mm^3$ | HB % | Leucocytic formula | | | | |
|---|---|---|---|---|---|---|---|---|---|---|
| | | | | | | linf. | monoc. | neutr. | eosin | bas |
| 6° + 6° | — | 0 | 7,30 ± 0,21 | 15,80 ± 1,30 | 14,87 ± 0,33 | 77,6 | 7,3 | 13,7 | 1,0 | 0 |
| 6° + 6° | — | 12 | 7,22 ± 0,19 | 16,72 ± 1,37 | 15,09 ± 0,37 | 76,2 | 8,8 | 14,4 | 0,6 | 0 |
| 6° + 6° | 5 | 0 | 7,83 ± 0,33 | 16,84 ± 0,90 | 15,20 ± 0,39 | 77,5 | 8,0 | 13,6 | 0,9 | 0 |
| 6° + 6° | 5 | 12 | 7,38 ± 0,21 | 17,04 ± 1,36 | 14,88 ± 0,36 | 77,6 | 7,9 | 13,6 | 0,9 | 0 |
| 6° + 6° | 10 | 0 | 7,21 ± 0,18 | 15,80 ± 1,39 | 14,86 ± 0,35 | 77,5 | 6,7 | 14,3 | 1,2 | 0 |
| 6° + 6° | 10 | 12 | 7,40 ± 0,20 | 16,70 ± 1,70 | 15,02 ± 0,42 | 77,8 | 9,4 | 12,1 | 0,7 | 0 |

TABLE 3
Chronic toxicity in rat : hematochemical tests

| Number of animals | mg/kg | Weeks of treatment | Glycemia mg/100 ml | Azotemia mg/100 ml | SGOT mU/ml | SGPT mU/ml |
|---|---|---|---|---|---|---|
| 6° + 6° | — | 0 | 78,7 ± 3,9 | 16,2 ± 0,7 | 11,9 ± 0,4 | 11,5 ± 0,6 |
| 6° + 6° | — | 12 | 84,5 ± 4,2 | 15,8 ± 0,6 | 13,2 ± 0,8 | 10,3 ± 0,7 |
| 6° + 6° | 5 | 0 | 79,6 ± 4,0 | 16,1 ± 0,6 | 12,6 ± 0,6 | 10,2 ± 0,5 |
| 6° + 6° | 5 | 12 | 87,8 ± 3,9 | 15,7 ± 0,5 | 12,9 ± 0,8 | 12,1 ± 0,6 |
| 6° + 6° | 10 | 0 | 78,5 ± 4,3 | 16,0 ± 0,6 | 11,7 ± 0,8 | 11,9 ± 0,5 |
| 6° + 6° | 10 | 12 | 80,3 ± 4,1 | 32,5 ± 1,6 | 12,3 ± 0,5 | 10,4 ± 0,7 |

TABLE 4
Chronic toxicity in rat : analysis of urine

| No. of animals | mg/kg | Proteins | Glucose | Bilirubin | Hemoglobin | Residue |
|---|---|---|---|---|---|---|
| 6° + 6° | — | 5(+),1 + | — | — | 2(+) | normal |
| 6° + 6° | 5 | 6(+) | — | — | 1(+) | normal |
| 6° + 6° | 10 | 7(+),2 | — | — | 2(+) | normal |

TABLE 5
Chronic toxicity in rat : relative average weight (mg/100 g of body weight) of some organs.

| Nr.aimals | mg/kg | Brain | Heart | Liver | Spleen | Loins |
|---|---|---|---|---|---|---|
| 6° + 6° | — | 598,5 ± 26,9 | 301,6 ± 11,6 | 3022 ± 88,5 | 298,8 ± 13,6 | 670,8 ± 33,4 |
| 6° + 6° | 5 | 579,6 ± 24,5 | 289,9 ± 11,2 | 3012 ± 101,6 | 304,2 ± 16,6 | 658,5 ± 26,4 |
| 6° + 6° | 10 | 583,7 ± 19,8 | 288,8 ± 11,3 | 3036,5 ± 79,8 | 303,7 ± 13,5 | 672,8 ± 29,6 |

3. Effects on the respiratory and on the cardiocirculatory activity as well as on the respiratory depression induced by morphine in rabbit. To perform these tests Towny Burgundy rabbits of both sexes have been used, weighing 2.7 – 3.2 kilos, hungry since about 15-18 hours, anaesthetized with ethyl uretane (1g/kg) and diallylbarbituric acid (40 mg/kg) by intravenous route.

The respiratory amplitude and frequency has been measured through a Battaglin-Rangoni poligraph. On the same polygraph the arterial pressure, the ECG and the cardiac frequency have been registered.

After stabilization of the respiratory and circulatory conditions and registration of the basic values, the compound PV1 has been administered by i.v. route at the doses of 1.25 - 2.5-5 mg/kg; equitossic doses of Dimefline have been also administered.

In another series of tests the administration of the drug has been preceded by the administration (i.v. route) of 10 mg/kg of morphine hydrochloride which has a depressing activity on the respiratory centers.

In the tests without previous administration of morphine the compound PV1 has constantly reduced the gradual diminution of the respiratory amplitude and frequency which spontaneously appears in the control animals, while has not affected the cardiocirculatory conditions.

In the tests performed under respiratory depression induced by morphine, the dose of 1.25 mg/kg has been uneffective to antagonize the intermittent breath of Sheyne-Stoches; the 2.5 mg/kg dose has been effective to reinstate normal values of respiratory amplitude and frequency, but needed repeated administration; the 5 mg/kg dose has been quite effective and only one administration was enough over a long period of time.

The cardiocirculatory conditions were not remarkably affected.

In all cases no convulsive phenomenon was detected.

The same tests performed with equivalent doses of Dimefline (equiactive doses) led to several cases showing convulsive phenomena.

4. Convulsivant effect on mouse.

This test has been performed on male Swiss mice weighing 20 - 22 g.

The mice, hungry since about 12 hours, have been subdivided in groups of 10 animals each and treated through gastric probe with PV1 and Dimefline. For PV1 the following dosages have been used: 30 - 45 - 60 - 75 mg/kg.

For each drug $CD_{50}$ (convulsivant dose for 50% of the animals) has been calculated, by using the statistic method of Litchfield and Wilcoxon (J. Pharmacol. 96, 99, 1949).

The obtained values are collected in Table 6.

As it may be seen the convulsivant effect starts at by far lower doses with Dimefline in comparison with the new drug PV1.

On the contrary, the stimulant action on the CNS indicated by the ratio $LD_{50}/CD_{50}$, is equivalent for the two drugs.

TABLE 6

| | Convulsivant effect of PV1 and Dimefline | | |
|---|---|---|---|
| Drug | $CD_{50}$ and L.F. mg/Kg | $LD_{50}$ and L.F. mg/Kg | $R(LD_{50}/CD_{50})$ |
| PV₁ | 58,0 (48,3–69,6) | 80,0 (61,6–104) | 1,38 |
| Dimefline | 8,9 (8,1–9,8) | 11,9 (10,3–13,8)* | |

*According to Setnikar and coll.

5. "Life-saving" effect.

This test indicates the activity of the considered drug against the toxicity of a barbiturate and is higly specific for analeptics in so far as bulbar stimulants, while other stimulants of the CNS such as amphetamine and strychnine do not modify the toxicity of the barbiturate or also raise the same (lobeline).

The test has been performed on male Swiss mice weighing 20–22 g, hungry since 15-18 hours, subdivided into 12 groups each comprising 10 animals.

The $LD_{50}$ of sodium pentobarbital has been determined by i.p. route on 40 mice.

Other two groups, each comprising 40 mice have been first administered with 13.4 mg/Kg of PV1 or with 2 mg/Kg of Dimefline and then with the sodium pentobarbital.

The $LD_{50}$ of pentobarbital has been in any case determined with the method of Litchfield and Wilcoxon.

The results are collected in the following Table 7.

TABLE 7

| Influence of PV1 and Dimefline on the toxicity of sodium Pentobarbital. | | |
|---|---|---|
| Drug | $LD_{50}$ and F.L. (mg/kg) | PR* |
| Pentobarbital | 108 (90–129,6) | — |
| Pentobarbital + PV₁(13,4 mg/Kg s.c.) | 150,0 (137,6–163,5) | 1,39 |
| Pentobarbital + Dimefline (2 mg/Kg s.c.) | 137,2 (123,6–152,3) | 1,27 |

*Ratio between the $LD_{50}$ of Pentobarbital with and without pre-treatment with the stimulant.

It is apparent that the compound PV1 reduces the toxicity of Pentobarbital much more than Dimefline, taking into account that the doses administered are equi-toxic doses.

Such a result accounts for a superiority of PV1 as analeptic.

By summing up, from the pharmacological tests performed (of which those above reported are only some significant ones), it results that the new componds according to the invention are very good analeptics, superior to the best analeptic presently known (Dimefline), and having the strong advantage with respect to Dimefline of being much less toxic, much less convulsivant and deprived of any side-effect.

I claim:

1. A compound of the formula

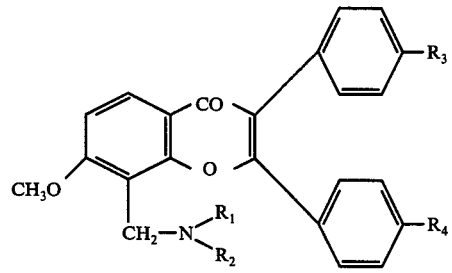

wherein $R_1$ and $R_2$ are both methyl or ethyl or taken together with the nitrogen atom to which they are attached represent morpholino, piperidino or pyrrolidino; $R_3$ and $R_4$ are always different and are hydrogen or methyl, and salts thereof.

2. A compound of claim 1 which is 7-methoxy-8-dimethylaminomethyl-2-(p-tolyl)isoflavone.

3. A compound of claim 1 which is 7-methoxy-8-morpholinomethyl-2-(p-tolyl)isoflavone.

4. A compound of claim 1 which is 7-methoxy-8-piperidinomethyl-2-(p-tolyl)isoflavone.

5. A compound of claim 1 which is 7-methoxy-8-pyrrolidinomethyl-2-(p-tolyl)isoflavone.

6. An analeptic composition comprising a therapeutically effective amount of a compound of claim 1, or a therapeutically acceptable acid addition salt thereof, in admixture with a therapeutically acceptable carrier.

* * * * *